United States Patent

Hsu et al.

[11] Patent Number: 6,004,265
[45] Date of Patent: Dec. 21, 1999

[54] VAGINAL SPECULUM WITH LIGHT GUIDE MEANS

[76] Inventors: Jin-cherng Hsu; Chen-Ke Hsu, both of 48, Yung Feng Road, Pa Te, Taoyuan Hsien, Taiwan

[21] Appl. No.: 09/260,355

[22] Filed: Mar. 1, 1999

[51] Int. Cl.⁶ .............. A61B 1/303; A61B 1/06
[52] U.S. Cl. ........................... 600/223; 600/220
[58] Field of Search .................. 600/220, 223, 600/241, 245

[56] References Cited

U.S. PATENT DOCUMENTS

| | | | |
|---|---|---|---|
| 672,239 | 4/1901 | Pilling | 600/220 |
| 1,150,749 | 8/1915 | Drosin | 600/220 |
| 2,247,258 | 6/1941 | Shepard | 600/241 |
| 3,349,764 | 10/1967 | Edinger et al. | 600/241 |
| 3,762,400 | 10/1973 | McDonald | 600/223 |
| 4,562,832 | 1/1986 | Wilder et al. | 600/223 |
| 4,597,382 | 7/1986 | Perez, Jr. | 600/220 |
| 4,638,792 | 1/1987 | Burgin | 600/223 |
| 5,007,409 | 4/1991 | Pope | 600/226 |
| 5,143,054 | 9/1992 | Adair | 600/223 |
| 5,319,009 | 6/1994 | Robinson | 600/241 |
| 5,499,964 | 3/1996 | Beck et al. | 600/220 |
| 5,785,648 | 7/1998 | Min | 600/223 |
| 5,873,820 | 2/1999 | Norell | 600/223 |

*Primary Examiner*—Paul J. Hirsch
*Attorney, Agent, or Firm*—Dougherty & Troxell

[57] ABSTRACT

A vaginal speculum having an upper blade and a lower blade pivoted together and adjusting screw means mounted operated to close/open the upper blade and the lower blade, wherein a longitudinally extended light guide is formed integral with an inside wall of the upper blade, having a rear end for connection to light source means by an optical fiber tube for guiding in light for illumination.

4 Claims, 4 Drawing Sheets

VAGINAL SPECULUM WITH LIGHT GUIDE MEANS

BACKGROUND OF THE INVENTION

The present invention relates to vaginal speculums, and more particularly to such a vaginal speculum which has light guide means for guiding in light from external light source means.

A vaginal speculum, or the so-called duck-bill, is an instrument for insertion into the vagina for inspection or medication. When a vaginal speculum is inserted into the vagina of a patient during an examination, a light source is needed to illuminate the inside of the vaginal speculum. When an external light source, for example, a projecting lamp at the examining table or a cap lamp at the cap worn on the head of the examiner is used to illuminate the inside of the vaginal speculum, the light of the light source tends to be blocked by the examiner's hands. There is another method of illuminating the inside of the vaginal speculum by positioning a fluorescent lamp tube in the rear opening of the vaginal speculum at the top. However, this method is not safe. Furthermore, a fluorescent lamp tube is not durable in use. Furthermore, regular vaginal speculums must be well sterilized before each use.

SUMMARY OF THE INVENTION

The present invention has been accomplished to provide a vaginal speculum which eliminates the aforesaid drawbacks. According to one aspect of the present invention, a solid light guide is formed integral with an inside wall of the upper blade of the vaginal speculum for connection to an external light source to guide light into the inside of the vaginal speculum. According to another aspect of the present invention, the solid light guide has a front slope for guiding out light uniformly in different directions. According to still another aspect of the present invention, the blades of the vaginal speculum are made of transparent material, therefore incidence light is never blocked by the blades. According to still another aspect of the present invention, an optical fiber tube is used to connect the light guide to an external light source, enabling light to be positively guided from the external light source to the inside of the vaginal speculum. According to still another aspect of the present invention, the vaginal speculum is cheap and disposable.

DETAILED DESCRIPTION OF THE PREFERRED EMBODIMENT

Figure 1:
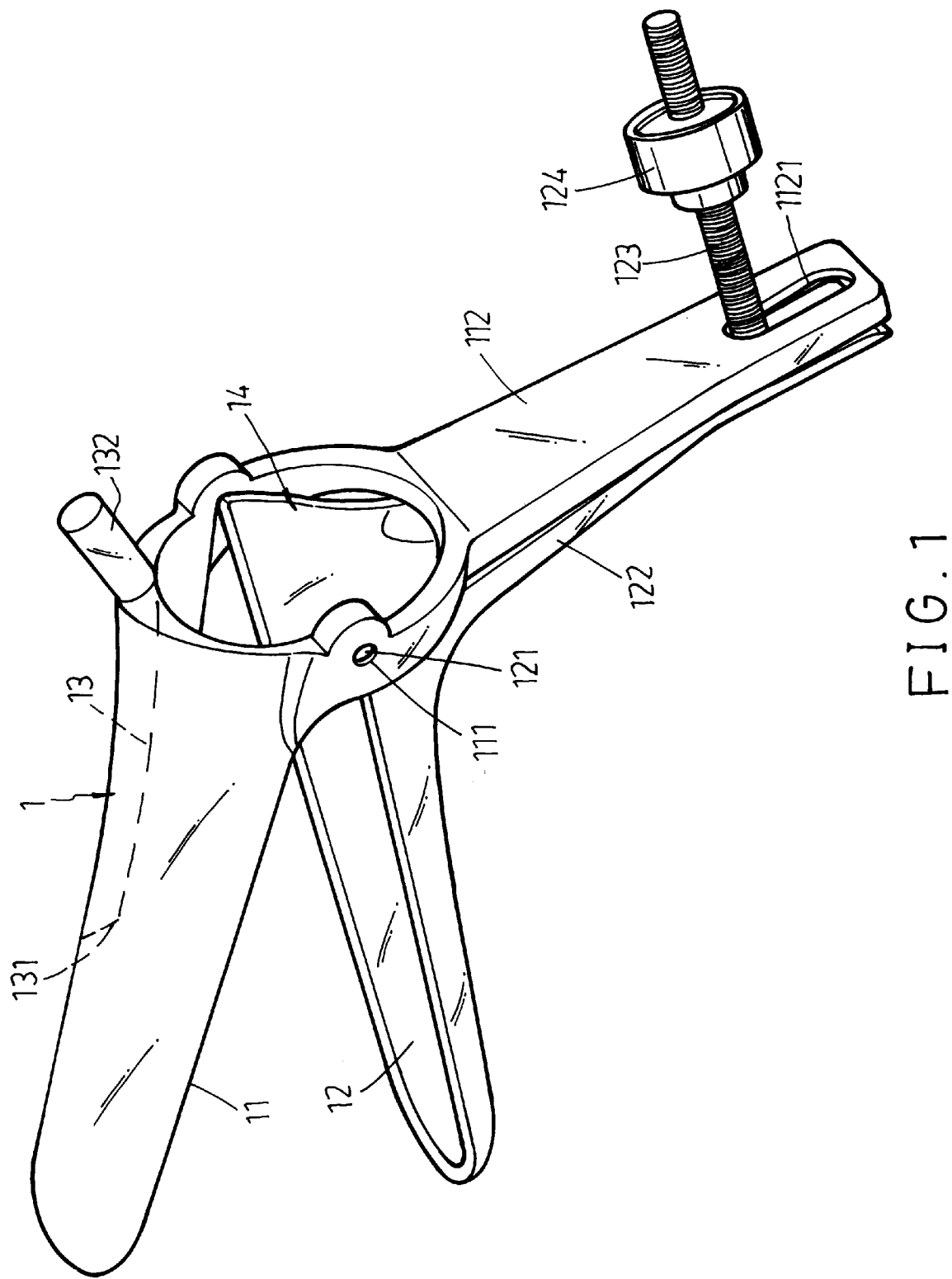
FIG. 1 is a perspective view of a vaginal speculum according to the present invention.
Figure 2:
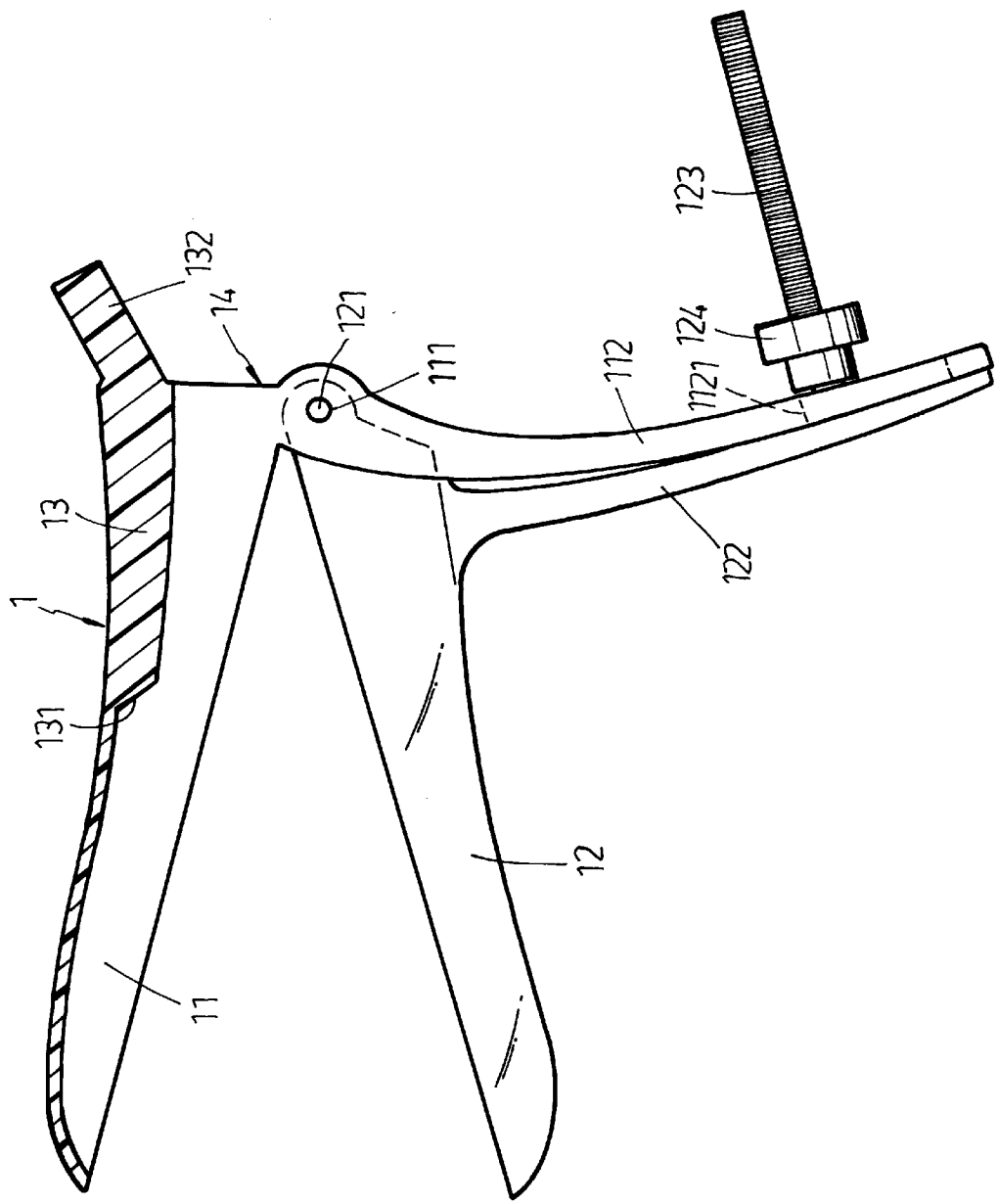
FIG. 2 is a sectional view of the vaginal speculum shown in FIG. 1.
Figure 3:
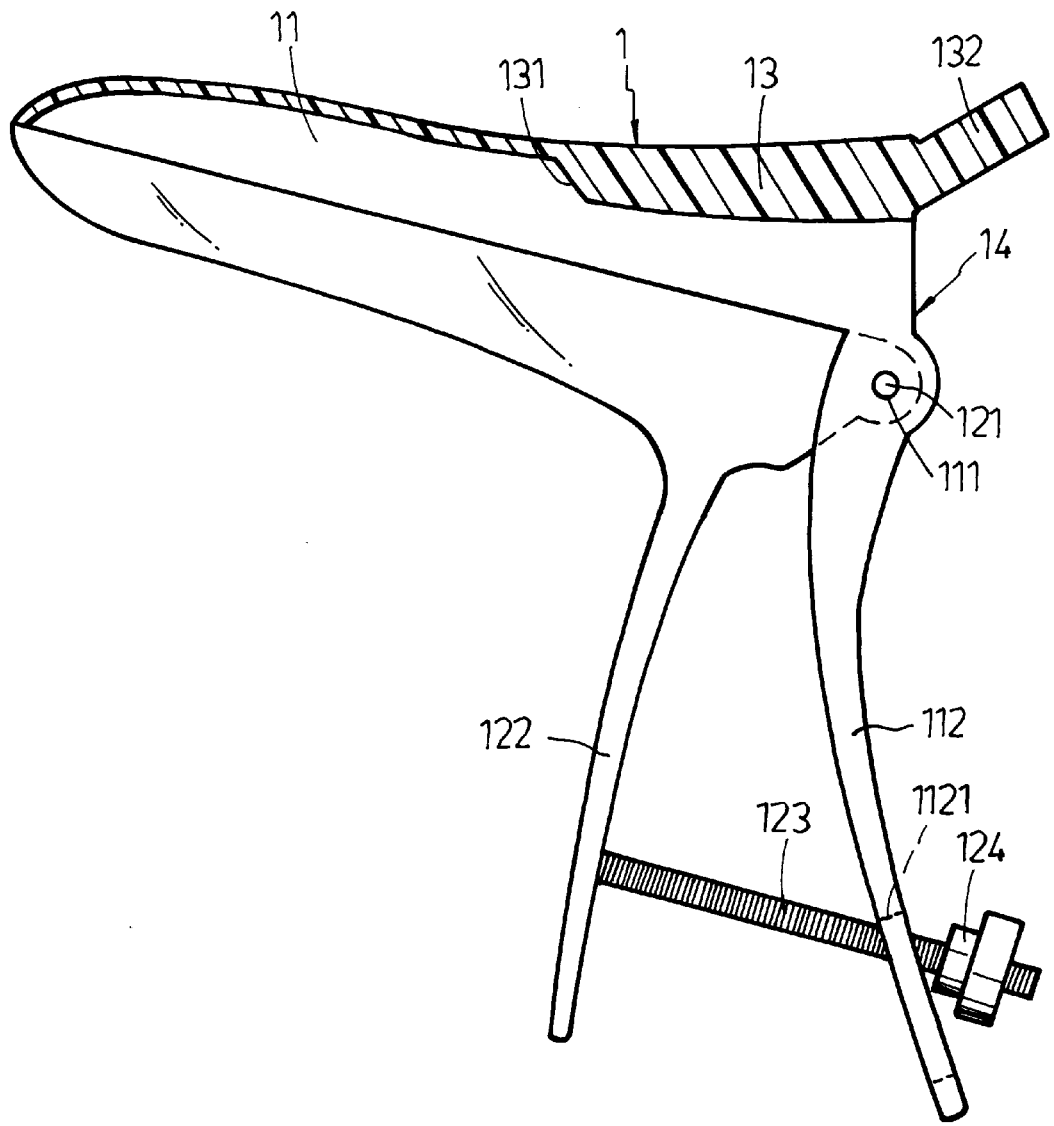
FIG. 3 is similar to FIG. 2 but showing the first blade and the second blade closed.

Referring to FIGS. from 1 through 3, a vaginal speculum 1 is shown comprised of a first blade 11 and a second blade 12. The first blade 11 and the second blade 12 each have a pair of pivot holes 111 bilaterally disposed at a rear side and pivotably coupled together by respective pivots 121, therefore the first blade 11 can be turned about the pivots 121 relative to the second blade 12. When the first blade 11 and the second blade 12 are fastened together, an opening 14 is defined within the blades 11 and 12 at the back side through which an examination implement can be inserted. The first blade 11 comprises a handle 112 extending downwardly from the rear end thereof at the bottom side. The handle 112 of the first blade 11 has an oblong slot 1121. The second blade 12 comprises a handle 122 extending downwardly from the rear end thereof at the bottom side. A locating screw rod 123 is mounted in the oblong slot 1121 at the handle 112 of the first blade 11 and stopped at the handle 122 of the second blade 12. An adjustment nut 124 is threaded onto the locating screw rod 123, and rotated to adjust the distance between the handle 112 of the first blade 11 and the handle 122 of the second blade 12. By means of adjusting the distance between the handle 112 of the first blade 11 and the handle 122 of the second blade 12, and the first blade 1 is closed on or opened from the second blade 12.

Figure 4:
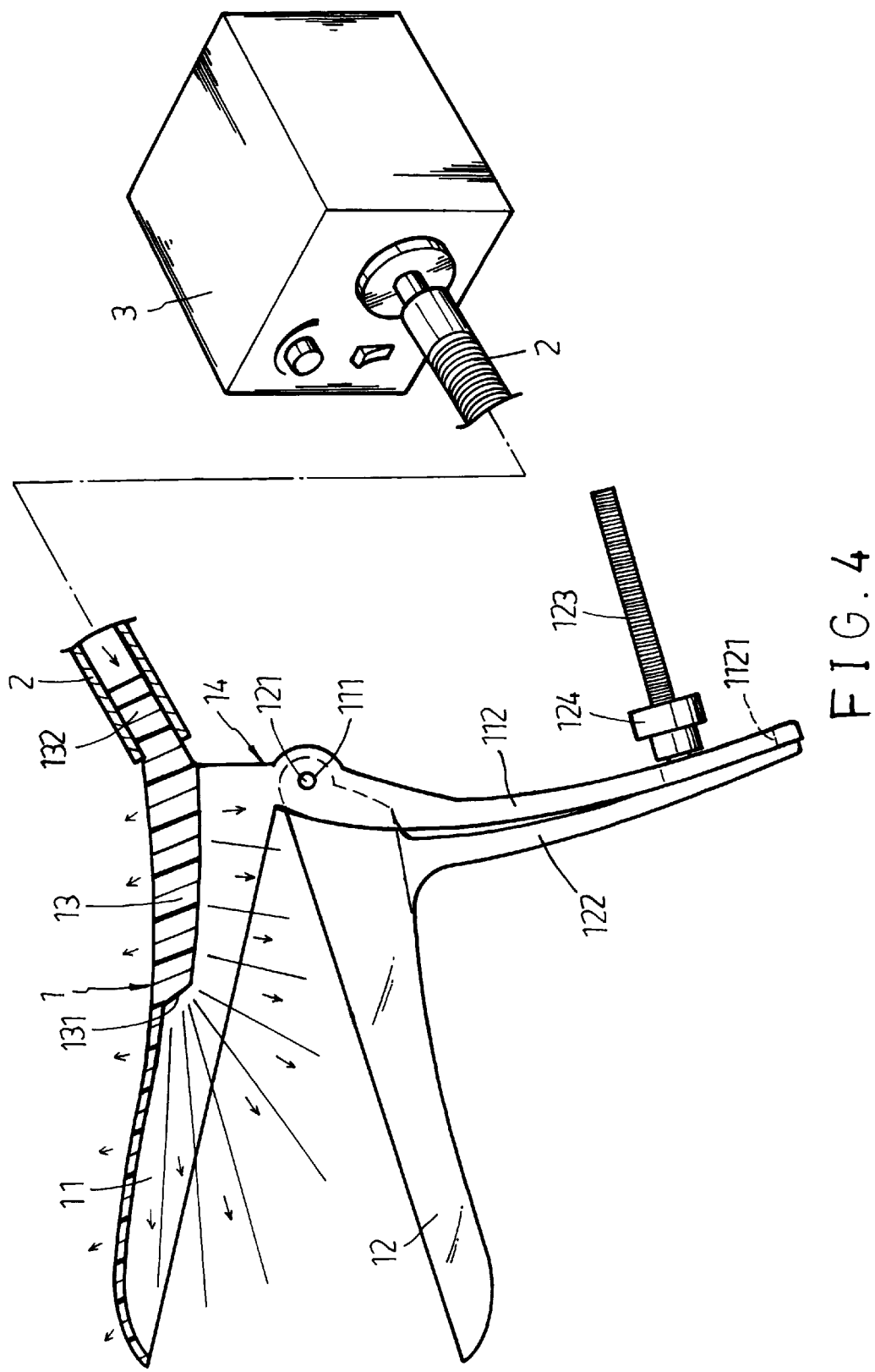
FIG. 4 shows an application example of the present invention.

Referring to FIG. 4 and FIGS. from 1 through 3 again, a solid light guide 13 is formed in integrity with an inside wall of the first blade 11, and longitudinally forwardly extending from the rear side at the opening 14 toward the front side. The light guide 13 comprises a front slope 131 at its front end, and a connecting portion 132 at its rear end. The connecting portion 132 projects obliquely upwards out of the opening 14 for connection to a lumin precision and examination light 3 through an optical fiber tube 2. When the lumin precision and examination light 3 is turned on, light is transmitted to the light guide 13 in the first blade 11 through the optical fiber tube 2, and guided out of the front slope 131 and the periphery of the light guide 13 to illuminate the space defined between the first blade 11 and the second blade 12. Further, the first blade 11 is light permeable. When light is guided through the light guide 13, the light guide 13 and the first blade 11 are simultaneously illuminated.

Further, the blades 11 and 12 are preferably injection-molded from transparent plastics so that the cost of the vaginal speculum can be greatly reduced.

What is claimed is:

1. A vaginal speculum comprising:
   a) first and second blades pivotally attached together, and forming a space therebetween as well as an opening at a back side thereof in communication with the space, the first and second blades being movable between opened and closed positions;
   b) an adjusting screw device operating on the first and second blades so as to hold the blades in a desired position; and,
   c) a transparent, solid light guide formed integrally with at least one of the first and second blades, the transparent solid light guide having a front surface sloped relative to an inner surface of the associated blade, a rear end forming a connecting portion projecting out of the opening for connection to a light source and a transparent periphery whereby light from the light source emanates from the sloped surface and the transparent periphery to illuminate the space between the first and second blades.

2. The vaginal speculum of claim 1, wherein the at least one blade having the transparent light guide is made of transparent material.

3. The vaginal speculum of claim 1, further comprising:
   a) a first handle extending from the first blade; and,
   b) a second handle extending from the second blade.

4. The vaginal speculum of claim 3, wherein the adjusting screw device comprises: a threaded screw rod extending from one of the first and second handles and through a slot in the other of the first and second handles; and an adjustment nut threaded onto the threaded screw rod.

* * * * *